United States Patent [19]

Zobrist et al.

[11] Patent Number: 4,879,289
[45] Date of Patent: Nov. 7, 1989

[54] METHOD OF AMELIORATING EPILEPTIC SEIZURES

[75] Inventors: Ray H. Zobrist; William R. Morrone, both of Olathe, Kans.

[73] Assignee: Marion Laboratories, Inc., Kansas City, Mo.

[21] Appl. No.: 198,054

[22] Filed: May 24, 1988

[51] Int. Cl.$^4$ .............................. A61K 31/55
[52] U.S. Cl. .................................. 514/211
[58] Field of Search ........................ 514/211

[56] References Cited

U.S. PATENT DOCUMENTS 4,567,175  1/1986  Takeda et al. .............. 514/211

OTHER PUBLICATIONS

Nagao et al., "Studies on a New 1,5-Benzothiazepine Derative . . . Pharmacological Properties," Japan J. Pharmacol., 22: 467-478 (1972).
Wauquier et al., "Calcium Entry Blockers as Cerebral Protecting Agents . . . ", Japan J. Pharmacol 38: 1-7 (1985).
Fischer et al., "On Influencing the Effectiveness . . . Electroconvulsion in Mice," Pharmazie 42 (6): 420-421 (1987).
Brodie et al., "Carbamazepine Neurotoxicity Precipitated by Diltiazem," Brit. Med. J., 292: 1170-71 (1986).
Shelton et al., "Induction of Seizures . . . BAY K 8644," Brain Res., 402: 399-402 (1987).
Ascioti et al., "Calcium Entry Blockers Anticonvulsant Drugs . . . ", Brit. J. Pharmacol., 88 (Suppl.): 379P (1986).

*Primary Examiner*—Stanley J. Friedman
*Attorney, Agent, or Firm*—Theresa M. Gillis

[57] ABSTRACT

A method for ameliorating or preventing generalized tonic-clonic type epileptic seizures in mammals is provided. The method involves systemically administering to a mammal in need of such treatment a compound having the formula

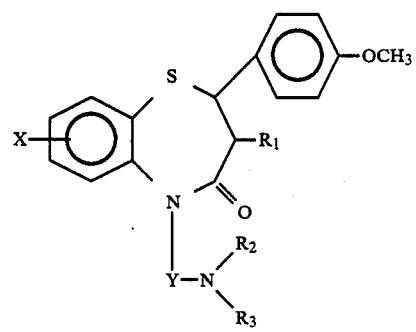

wherein X is hydrogen, a lower straight chain or branched alkyl, hydroxy, a halogen or a lower straight chain or branched alkyl halide; Y is a lower straight chain or branched alkyl; $R_1$ is hydrogen, hydroxy or acetyloxy; $R_2$ and $R_3$ are each a lower straight chain or branched alkyl or a non-aromatic cycloalkyl or together are a heterocyclic, and pharmaceutically acceptable salts thereof in an amount effective to ameliorate or prevent generalized tonic-clonic type seizures. Preferred compounds are those in which X is hydrogen or 8-chloro, Y is ethyl, $R_1$ is acetyloxy and $R_2$ and $R_3$ are each methyl. Most preferred compounds include (+)(2S,3S)-3-acetyloxy-5-(2-dimethylaminoethyl)-2,3-dihydro-2-(4-methoxyphenyl) 1,5-benzothiazepin-4-(5)-one and (+)(2S,3S)-3-acetoxy-8-chloro-5-(2-dimethylaminoethyl)-2,3-dihydro-2-(4-methoxy phenyl)-1,5-benzothiazepin-4-(5H)-one.

10 Claims, 4 Drawing Sheets

METHOD OF AMELIORATING EPILEPTIC SEIZURES

BACKGROUND OF THE INVENTION (a) Field of Invention

The invention relates to a method for ameliorating or preventing generalized tonic-clonic type seizures associated with epilepsy which involves systemically administering to a mammal in need of such treatment a benzothiazepine calcium channel antagonist in an amount effective to prevent or ameliorate such seizures.

(b) State of the Art

Abnormal electrical discharges can arise in the brain due to various electrical or chemical stimuli. Certain regions of the brain including the temporal lobe and the deep nuclear aggregates of the motor cortex, the amygdala and the hippocampal structures of the limbic system are particularly sensitive to abnormal electrical discharges. An alteration in membrane permeability to extracellular calcium appears to be a critical event in the genesis of these abnormal electrical discharges and probably precedes paroxysmal neuronal discharge associated with epileptic seizures.

Epilepsy is a collective designation for a group of central nervous system disorders having in common the spontaneous occurrence of seizures associated with the disturbance or loss of consciousness. These seizures are usually, but not always, associated with characteristic body movements (convulsions) and sometimes autonomic hyperactivity. Seizure in epilepsy detonation is believed to originate in the non-specific subcortical mesodiencephalic reticular systems and diffuse bilaterally into the cerebral cortex. The motor cortex, the amygdala and the hippocampus have a low threshold and high susceptibility to seizure possibly due to the vulnerability of their vasculature to compression and biochemical disturbances. See, e.g., Glaser, "The Epilepsies," *Textbook of Medicine*, Beeson and McDermott, eds., W B Saunders Co., Philadelphia, 1975, pp. 723-24.

Epileptic seizures are divided into partial and generalized seizures on the basis of the clinical manifestations of the attacks and the electroencephalographic (EEG) pattern. Each of these two general epileptic categories is then further subdivided into three or more subcategories depending on the classification scheme employed as shown in Table I. Accurate diagnosis is therefore essential since pharmacotherapy is highly selective for a particular type of epileptic seizure.

TABLE I

International Classification of Epileptic Seizures[1, 2]

I. Partial seizures (beginning locally)
  A. Simple partial seizures (consciousness not impaired)
    1. With motor symptoms
    2. With somatosensory or special sensory symptoms
    3. With autonomic symptoms
  B. Complex partial seizures (with impairment of consciousness)
    1. Beginning as simple partial seizures and progressing to impairment of consciousness
      a. With no other features
      b. With features as in simple partial seizures
      c. With automatisms
    2. With impairment of consciousness at onset
      a. With no other features
      b. With features as in simple partial seizures
      c. With automatisms
  C. Partial seizures secondarily generalized
II. Generalized seizures (bilaterally symmetrical, without local onset)
  A. 1. Absence seizures
     2. Atypical absence seizures
  B. Myoclonic seizures
  C. Clonic seizures
  D. Tonic seizures
  E. Tonic-clonic seizures
  F. Atonic seizures
III. Unclassified epileptic seizures (data inadequate or incomplete)

[1]Approved by the International League Against Epilepsy in September 1981
[2]ref. Porter et al., Cleve. Clin. Q. 51:293-305, 1984.

Changes in free intracellular calcium ion ($Ca^{2+}$) levels provide a signal allowing muscle and nerve cells to respond to a variety of external stimuli. For example, neurotransmitter release is specifically dependent on $Ca^{2+}$ entry into neurons. Membrane permeability to extracellular $Ca^{2+}$ may also be a factor preceding neuronal discharge and seizure appearance. Recent studies have now suggested that the flux of extracellular $Ca^{2+}$ into neurons may be directly related to the development of epileptic seizures. See, e.g., Pumain et al., Science 222:177-179, 1983; Schwartzkroin et al., Ann. Neurol. 7:95-107, 1980.

For example, Shelton et al., Brain Res. 402: 399-402, 1987, induced epileptic-like seizures in mice by the non-systemic direct intracerebroventricular administration of BAY k8644, a calcium channel activator. Also, known anticonvulsant drugs, such as phenytoin, which are used in treating epilepsy can affect $Ca^{2+}$-dependent mechanisms in neurons. Phenytoin has been shown to reduce $Ca^{2+}$ uptake by neurons, as well as inhibit $Ca^{2+}$-dependent guanosine-3',5'-monophosphate synthesis and protein phosphorylation. The inhibition of $Ca^{2+}$ flux in neurons by phenytoin may be through its binding to $Ca^{2+}$ channel regulatory proteins, since phenytoin has been shown to inhibit the binding of nitrendipine, a known $Ca^{2+}$ channel antagonist, to neuronal membranes. See, e.g., Harris et al., Biochem. Pharmacol. 34:2187-2191, 1985.

Calcium influx into cells is mediated by $Ca^{2+}$ channels which are proteins that span the cell membrane to provide an aqueous route for passage of ions into cells. See e.g., Greenberg, Ann. Neurol. 21:317-330, 1987, for a review. $Ca^{2+}$ flux through $Ca^{2+}$ channels is believed to be a passive process merely requiring that the channels be open to permit $Ca^{2+}$ ions to descend an electrochemical gradient into the cells. Two broad classes of $Ca^{2+}$ channels are known: (1) Voltage-dependent $Ca^{2+}$ channels activated to open by membrane depolarization and (2) so-called receptor-operated $Ca^{2+}$ channels, which open as a result of ligand-binding to specific cell-surface receptors. However, significant $Ca^{2+}$ channel heterogeneity exists, based on differences in membrane potentials required to open the channels, tendency to inactivate and pharmacologic sensitivity. Furthermore, a subpopulation of $Ca^{2+}$ channels in neurons of the central nervous system (CNS) appear to be pharmacologically distinct from $Ca^{2+}$ channels found in peripheral tissues. See e.g., Scriabine et al., in *New Drugs Annual*, ed. A. Scriabine, Raven Press, New York, pp. 197-218, 1985.

The flux of Ca²⁺ ions through Ca²⁺ channels can be inhibited by a diverse group of organic compounds termed Ca²⁺ channel antagonists. Four chemical classes of Ca²⁺ channel antagonists have been generally recognized: (1) the dihydropyridines, exemplified by nifedipine and nimodipine; (2) the phenylalkylamines, such as verapamil; (3) the benzothiazepines, such as diltiazem; and (4) the diphenylalkylamines, such as flunarazine.

Ca²⁺ channel antagonists show a high degree of specificity, both structurally and sterically. Many Ca²⁺ channel antagonists are highly stereospecific, in that one of two optical isomers can be substantially more potent than the other. Furthermore, it has been shown that minor structural alterations can change a Ca²⁺ channel antagonist into a Ca²⁺ channel activator which actually enhances Ca²⁺ influx. For example, it has been shown with certain dihydropyridine compounds that one isomer can block Ca²⁺ influx while the other isomer stimulates Ca²⁺ flux. See, e.q., Franckowiak et al., Eur. J. Pharmacol. 114:223-226, 1985; Kongsamut et al., Biochem. Biophys. Res. Commun. 130:141-148, 1985. In addition, certain calcium channel antagonists are believed to be CNS-selective, whereas others are less specific for Ca²⁺ channels in CNS neurons. See, e.g., Scriabine et al., supra. For example, nimodipine is known to be selective for CNS neurons whereas verapamil is not. See e.g., Meyer et al., Mayo Clin. Proc. 61:239-247 1987; Schwartz et al., Ann. Rev. Med. 35:325-339, 1984. The CNS selectivity of other calcium channel antagonists, such as the benzothiazepines, is as yet undefined.

Generally, this diverse group of Ca²⁺ channel antagonists has been therapeutically categorized as vasodilators and have found wide clinical use in treatment of cardiovascular problems, such as angina, and hypertension. Because of the suggested relationship between Ca²⁺ influx into neurons and the development of epileptic seizures, it is believed that inhibition of Ca²⁺ flux by Ca²⁺ channel antagonists may be therapeutically useful, either alone or as adjuvants to traditional anticonvulsant drugs, in treating epileptic seizures.

Various studies have suggested that Ca²⁺ channel antagonists, by themselves, possess no anticonvulsant activity. For example, the d, dl and 1-cis isomers of diltiazem were shown to have no anti-chemoshock or anti-electroshock activity, even at doses of 200 mg/kg, p.o. See, e.g., Nago et al., Japanese J. Pharmacol. 2:467-478, 1972. More recent studies have demonstrated that Ca²⁺ channel antagonists per se, e.g., cinnarizine nifedipine, nimodipine, diltiazem and verapamil, had no anti-epileptic activity in mice as measured with the maximal electroshock test. See, e.g., Fisher et al., Pharmazie 42:420-421, 1987.

Some studies have suggested, however, that certain Ca²⁺ channel antagonists may augment the effects of traditional anticonvulsant agents. See, e.g., Shelton et al., Brain Res. 402:399-402, 1987. There is some evidence in animal epileptic model systems and in minimal clinical studies that specific dihydropyridine and diphenylalkylamine Ca²⁺ channel antagonists, especially those with CNS-selectivity, may be effective antiepileptic agents, particularly if such agents are used as adjuvant therapy to known anticonvulsant drugs. See e.g., Greenberg, supra; Speckman et al., Funct. Neurol. 1:521-527, 1986; Ascioti et al., Brit. J. Pharmacol. 88 (Suppl.):374 p., 1986; Meyer et al, supra; Van Der Bussche et al., in *Calcium Entry Blockers and Tissue Protection*, Godraind et al., eds., Raven Press, New York, pp. 229-236, 1985; Shelton et al., supra; Fischer et al., Pharmazie 42:420-421, 1987; Desmedt et al., Arzneimithelforschung 25:1408-1413, 1975; Waquier et al., Japan J. Pharmacol. 38:1-7, 1985; Larkin et al., Brit. Med. J. 296:530-531, 1988. No studies to date, however, have demonstrated positive anticonvulsant activities for the benzothiazepine class of Ca²⁺ channel antagonists.

That Ca²⁺ channel antagonists may have anticonvulsant activity is especially important since the currently available antiepileptic drugs are not only ineffective in many patients, but can frequently cause side effects ranging in severity from minimal CNS impairment to, in rare cases, death due to aplastic anemia or hepatic failure. Furthermore, administration of certain antiepileptic drugs, e.g., phenytoin, to pregnant epileptic women may result in the production of birth defects in the children, i.e., the so-called "Dilantin Syndrome." On the other hand, Ca²⁺ channel antagonists, as a class of drugs, have been shown to possess minimal neurolgogic and physiologic side effects. See, e.g., Chaffman et al., Drugs 29:387-454, 1985. Thus, Ca²⁺ channel antagonists, especially those with CNS-selectivity, may be useful antiepileptic drugs.

SUMMARY OF THE INVENTION

A method for ameliorating generalized tonic-clonic type epileptic seizures in mammals suffering from such seizures has now been found. The method involves systemically administering to mammals suffering from generalized tonic-clonic type seizures a benzothiazepine compound having calcium channel antagonist activity in an amount effective to ameliorate generalized tonic-clonic type epileptic seizures.

The invention thus is a method of ameliorating generalized tonic-clonic type epileptic seizures in a mammal by systemically administering to a mammal in need of such treatment a compound having calcium antagonist activity and the formula:

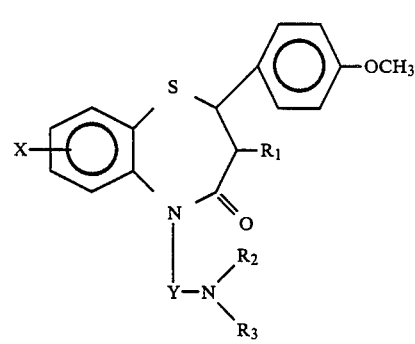

wherein X is hydrogen, a lower straight chain or branched alkyl, hydroxy, a halogen or a lower straight chain or branched alkyl halide; Y is a lower straight chain or branched alkyl; R₁ is hydrogen, hydroxy or acetyloxy; R₂ and R₃ are each a lower straight chain or branched alkyl or a non-aromatic saturated or unsaturated cycloalkyl having no more than 6 carbon atoms or together are a heterocyclic, and pharmaceutically acceptable salts thereof in an amount effective to ameliorate generalized tonic-clonic type seizures. The term "lower" used in conjunction with an alkyl group herein is intended to mean one having no more than 8 carbon atoms. By "heterocyclic" is meant a single ring, preferably saturated, having no more than 6 carbon atoms. In the practice of the invention, the compound of formula I may be systemically administered to the mammal orally or by injection. Effective amounts will range from about 0.5 to 360 mg of the benzothiazipine compound (I) administered per day.

In a preferred embodiment, the invention provides a method for ameliorating or preventing generalized tonic-clonic type seizures in a mammal by use of an effective amount of a benzothiazepine calcium channel antagonist which selectively inhibits $Ca^{2+}$ entry into neurons of the central nervous system (CNS). Most preferred compounds for use in the invention include (+)(2S,3S)-3-acetyloxy-5-(2-dimethylaminoethyl)-2,3-dihydro-2-(4-methoxyphenyl)-1,5-benzothiazepin-4-(5H)-one (herein, diltiazem) and (+)(2S,3S)-3-acetyloxy-8-chloro-5-(2-dimethylaminoethyl)-2,3-dihydro-2-(4-methoxyphenyl)-1,5-benzothiazepin-4-(5H)-one (herein designated TA-3090).

DETAILED DESCRIPTION OF THE INVENTION

Figure 1:
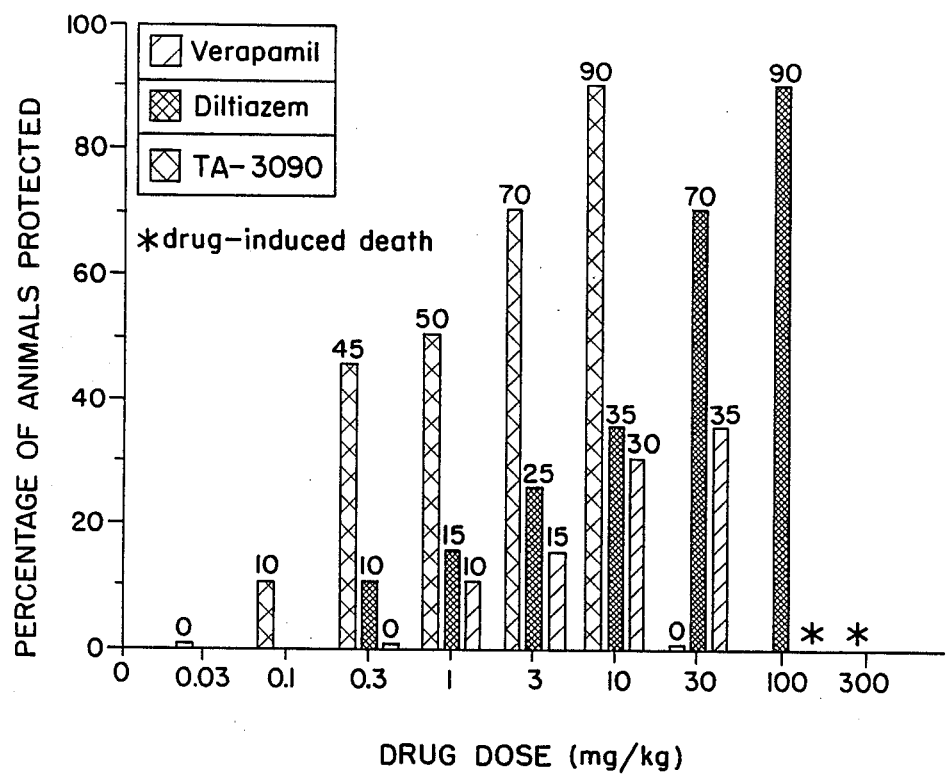
FIG. 1 is a graph showing protection from MES-induced seizures after intraperitoneal administration of benzothiazepine compounds.

The present invention provides a method for preventing or ameliorating generalized tonic-clonic type epileptic seizures in mammals, commonly human patients, suffering from such seizures. The method involves administering to a mammal suffering from generalized tonic-clonic type epileptic seizures a compound having the formula

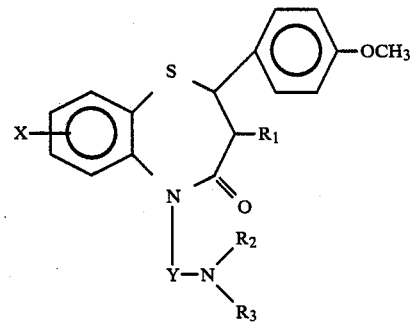

I wherein X is hydrogen, a lower straight chain or branched alkyl, hydroxy, a halogen or a lower straight chain or branched alkyl halide; Y is a lower straight chain or branched alkyl; $R_1$ is hydrogen, hydroxy or acetyloxy; $R_2$ and $R_3$ are each a lower straight chain or branched alkyl or a non-aromatic saturated or unsaturated cycloalkyl having no more than 6 carbon atoms or together are a heterocyclic, and pharmaceutically acceptable salts thereof in an effective amount. The term "lower" used in conjunction with an alkyl group herein is intended to mean one having no more than 8 carbon atoms. By "heterocyclic" is meant a single ring, preferably saturated, having no more than 6 carbon atoms. Effective amount means the amount necessary to at least ameliorate, and optimally prevent, generalized tonic-clonic type seizures. Similarly, amelioration of seizures refers to all degrees of amelioration, including complete prevention.

Preferably, the compound of formula I is a benzothiazepine calcium channel anagonist which selectively inhibits the influx of $Ca^{2+}$ ions into neurons of the central nervous system (CNS). In the preferred compounds useful in the invention, Y is ethyl, X is hydrogen or chloro, $R_1$ is acetyloxy, and $R_2$ and $R_3$ are each a lower alkyl, most preferably methyl. Most preferred compounds for use in the practice of the invention include diltiazem in which Y is ethyl, X is hydrogen, $R_1$ is acetyloxy, and $R_2$ and $R_3$ are each methyl and TA-3090 in which Y is ethyl, X is 8-chloro, $R_1$ is acetyloxy, and $R_2$ and $R_3$ are each methyl. Most preferred forms of these compounds for use in the invention include the hydrochloride salt of diltiazem and the maleate salt of TA-3090. In addition, certain metabolites of diltiazem, e.g., desacetyldiltiazem (herein designated Ml) which results from the oxidative deacetylation at position 3 ($R_1$) of diltiazem, are also active and useful in the invention.

Diltiazem and TA-3090 surprisingly have proven effective in ameliorating or preventing seizures in the maximal electroshock convulsion (MES) test in mice. The MES test is recognized as a model for generalized tonic-clonic type epileptic seizures and drugs which are effective in the MES test are usually clinically effective in treating such epileptic forms. See, e.g., Swinyard et al., ISI Atlas of Pharmacology, in press, 1988. The appearance of tonic hind limb extensions (THE) or death in the MES indicates a lack of protection against generalized tonic-clonic type epileptic seizures. Diltiazem and TA-3090 were both effective in protecting mice against the appearance of THE and/or death in the MES test after both oral and intraperitoneal administration. The results were surprising in that diltiazem and TA-3090 are not known to enter the central nervous system in quantities sufficient to produce pharmacologic activity. In concurrent testing, verapamil, which is not CNS-specific, afforded relatively little protection in the MES tests. Furthermore, previous studies have shown that, in contrast to diltiazem and TA-3090, oral administration of the CNS-selective dihydropyridine calcium channel antagonist nimodipine was ineffective against MES-induced seizures but protected against pentylenetetrazole-induced seizures (a model for absence seizures). See, e.g., Hoffmeister et al., Arzneimittelforschung 32:347–360, 1982.

The invention is thus particularly directed to treating generalized tonic-clonic type epileptic seizures. Since benzothiazepine $Ca^{2+}$ channel blockers have been rarely reported to produce adverse side effects during normal usage, it is believed that the invention will afford a high level of seizure control in mammals, without the toxic side effects often produced by known anticonvulsant drugs used to treat epileptic seizures.

The benzothiazepine compounds (I) used in the practice of the invention may be systemically administered orally or by injection. Total unit daily dosages or therapeutically effective quantities can vary over a wide range, for instance, from about 0.5 to about 360 mg per day depending on the factors provided below. A suitable total daily dose of the benzothiazapine compound (I) or pharmaceutically acceptable salt thereof preferably varies from about 30 to 180 mg per day, preferably divided into several doses. Conveniently, the total unit daily dosage of the benzothiazepine (I) compound is administered to the patient in three to four equally divided daily doses.

As with known anticonvulsant drugs used to ameliorate or prevent epileptic seizures, it will be appreciated by those skilled in the art that the particular benzothiazepine $Ca^{2+}$ channel antagonist of formula I chosen and the specific route and timing of administration of the compound to ameliorate or prevent generalized tonic-clonic type epileptic seizures in a mammal are factors in determining the therapeutically effective amount of the drug to be administered in the practice of the present invention. Other conditions which may affect the amount of compound to be administered include the severity of the epileptic condition, whether generalized tonic-clonic type epileptiforms are present, the age, sex and general physical condition of the patient, and whether the benzothiazepine compound (I) will be used in conjunction with a known anticonvulsant drug, such as phenytoin or phenobarbital.

The benzothiazepine compounds (I) may be administered in the form of pharmaceutical preparations containing the compounds admixed with pharmaceutically acceptable carriers suitable for parenteral or oral administration. Preferably the compounds will be orally administered as tablets, capsules, powders or in liquid form such as suspensions, solutions, emulsions or syrups. When formed into tablets, conventional excipients (e.g., sodium citrate, lactose, microcrystalline cellulose, starch), lubricating agents (e.g., anhydrous silicic acid, hydrized castor oil, magnesium stearate, sodium lauryl sulfate, talc) and binding agents (e.g., starch paste, glucose, lactose, gum acacia, gelatin, mannitol, magnesium trisilicate, talc) can be used. When administered as liquids, conventional liquid carriers can be employed. In the case of solid preparations, each unit dosage form of the active ingredient can contain from about 5 to 95% of the same by weight based on the entire composition with the remainder comprising conventional pharmaceutical carriers. When the therapeutic agent is used as an aqueous solution, i.e., injection, the solution may contain from about 0.05 to 5.0% of same by weight based on the entire solution.

In a preferred embodiment of the invention, diltiazem is systemically administered to a mammal suffering from generalized tonic-clonic type epileptic seizures. Diltiazem, which is widely used to treat cardiovascular problems, including hypertension, may be readily obtained from commercial sources, e.g., Marion Labs, for use in the invention or prepared according to the method disclosed in U.S. Pat. No. 4,438,035. For amelioration or prevention of generalized tonic-clonic type epileptic seizures, diltiazem, preferably in its hydrochloride form, is admixed with a pharmaceutically acceptable carrier and administered to a mammal who suffers from such seizures and is in need of treatment.

Diltiazem may be formulated for administration orally or by injection as indicated above. Preferably patients will be maintained on oral total daily dosages of about 0.5 to 360 mg, preferably about 30 to 180 mg per day, in divided doses to ameliorate or prevent epileptic seizures. If the compound is administered after the onset of seizures, the preferred route is by injection. Effective i.v. dosage amounts of the compound will be lower than those for oral administration. It is well within the skill of the treating physician to determine the amount of the compound which will ameliorate seizures in a given patient.

Diltiazem, preferably in the hydrochloride form, has been shown to be effective in protecting against generalized tonic-clonic type epileptic seizures in an animal model of epilepsy when administered in a single undivided dose orally or by peritoneal injection, in an amount ranging from about 0.3 to 200 mg per kg body weight. The most effective dose range in the mouse model appeared to be about 50 to 200 mg per kg of body weight. When orally administered, a dose of about 200 mg per kg body weight has been shown to afford excellent protection against experimentally induced tonic-clonic seizures. Maximal protection against these seizures appears to be about 60 minutes following oral administration of diltiazem, with a time range of protection between about 15–300 minutes.

In a second preferred embodiment, the benzothiazepine $Ca^{2+}$ channel antagonist used in the method of the invention is the compound TA-3090, preferably administered as a maleate salt. The considerations for the particular formulation, route of administration of TA-3090 and determining the therapeutically effective amount of the compound are the same as for diltiazem. In general, the therapeutically effective amount of TA-3090 will be lower than that of diltiazem. TA-3090 administered intraperitoneally proteced against experimentally produced generalized tonic-clonic type epileptic seizures in animal models in a dose range of about 0.1 to 20 mg per kg body weight, with the most effective dose being about 10 mg per kg body weight. Oral administration of about 30 mg per kg body weight of TA-3090 also provided very good protection against experimentally-produced generalized tonic-clonic type epileptic seizures. Maximum protection following oral administration of TA-3090 was seen at about 60 minutes following oral drug administration, with good protection until about 180 minutes post-administation. TA-3090 affords some protection as early as 15 minutes and as long as 300 minutes following oral administration.

It is believed that the benzothiazepine compounds (I) of the invention not only will be useful in the treatment of generalized tonic-clonic type epileptic seizures with the aforementined reduction in side effects, but also may prove useful in providing treatment of certain individuals suffering from epileptic seizures for whom treatment has heretofore proved ineffective.

The invention is further illustrated by the following specific examples which are not intended in any way to limit the scope of the invention.

EXAMPLE 1

The calcium channel antagonists diltiazem, TA-3090, and verapamil were tested to determine their efficacy following intraperitoneal injection in inhibiting artificially induced convulsive episodes in two models of epilepsy, i.e., the MES test and the maximal Metrazol (pentylenetetrazole) convulsion (MMC) test in mice. The known anticonvulsant agents phenytoin and valproic acid were used in the MES and MMC tests, respectively, as positive controls.

For each of the MES and MMC tests, male Swiss-Webster mice (20–30 gm) were randomly divided into 5 groups, weighed, and treated as follows:

GROUP A: Normal saline or vehicle as negative control, 1% of body weight, i.p.

GROUP B: MES; Phenytoin as positive control in MES test, 20 mg/kg, i.p.; Valproic acid as positive control in MMC test, 175 mg/kg, i.p. (Sigma Chemical Co., St. Louis, Mo.)

GROUP C: Diltiazem, 0.3-300 mg/kg, i.p. (Marion Lot #41596)

GROUP D: TA-3090, 0.03-30 mg/kg, i.p. (Marion Lot #503010)

GROUP E: Verapamil, 0.3-300 mg/kg, i.p. (Sigma Chemical Co., St. Louis Mo.)

The tests were then carried out as follows:

MAXIMAL ELECTROSHOCK CONVULSION TEST (MES): Each compound was administered as indicated above. Seizure was induced in the mouse 20 minutes after drug administration by the corneal application of a 40 mA electrical current for 0.2 seconds. The appearance of tonic hindlimb extensions (THE), or death, was considered lack of protection.

MAXIMAL METROZOL CONVULSION TEST (MMC): Each test compound was administered as indicated above. Twenty minutes later, Metrazol (pentylenetetrazole, 85 mg/kg) was subcutaneously administered to each animal. The animal was then observed for an additional 30 minutes for the absence or incidence of forelimb clonic convulsions. Clonic convulsive episodes of 5 seconds or more duration were considered lack of protection.

Following each test, the mice were immediately sacrificed by cervical dislocation either 10 seconds after the appearance of convulsions or 30 minutes post-Metrazol or electroshock administration, whichever came first. Protection against convulsions was recorded as a quantal (all or none) response. To determine the dose at which 50% of the animals were protected ($ED_5$), seven half-logarithmetically-spaced doses of the test compounds were administered to groups of 10-20 animals. The $ED_{50}$ dose was obtained by probit analysis.

The effects of intraperitoneally administered diltiazem, TA-3090, and verapamil on the incidence of MES-induced seizures are shown in FIG. 1 and Table II. FIG. 1 is a bar graph showing the relative protective activities of the various test compounds against electroshock-induced seizures in the mouse. The number above each bar represents the percentage of animals protected against tonic seizures.

TABLE II

EFFECTS OF DILTIAZEM, TA-3090, AND VERAPAMIL IN THE MAXIMAL ELECTROSHOCK CONVULSION TEST[3, 4]

| Dose mg/kg | Diltiazem % Protected[1] | P/T[2] | TA-3090 % Protected | P/T | Verapamil % Protected | P/T |
|---|---|---|---|---|---|---|
| 0.03 | | | 0 | 0/10 | | |
| 0.1 | | | 10 | 2/20 | | |
| 0.3 | 10 | 2/20 | 45 | 9/20 | 0 | 0/10 |
| 1 | 15 | 3/20 | 50 | 10/20 | 10 | 2/20 |
| 3 | 25 | 5/20 | 70 | 14/20 | 15 | 3/20 |
| 10 | 35 | 7/20 | 90 | 18/20 | 30 | 6/20 |
| 15 | | | 50 | 5/10 | | |
| 20 | | | 40 | 4/10 | | |
| 30 | 70 | 14/20 | 0 | 0/10 | 35 | 7/20 |
| 100 | 90 | 18/20 | | | * | * |
| 200 | 100 | 9/9 | | | | |
| 300 | * | * | | | * | * |

[1]Percentage of animals protected from tonic hindlimb seizures.
[2]Number of animals protected/number of animals tested.
[3]Negative Saline Control (<0.3 cc) 0% (0/25).
[4]Positive Phenytoin Control (20 mg/kg) 100% (10/10).
*100% death due to drug.
Drug not tested at this dose.

It is apparent from the data in FIG. 1 and Table II that both diltiazem and TA-3090 protected the mice from seizures in a dose-dependent fashion, with TA-3090 being approximately ten (10) times more potent than diltiazem. Probit analysis of the data revealed $ED_{50}$ values of 10.96 mg/kg and 0.84 mg/kg for diltiazem and TA-3090, respectively. Diltiazem and TA-3090 therefore appear to be of at least equal efficacy to phenytoin ($ED_{50}$=9.5 mg/kg[5]) in preventing THE in the MES test in the mouse. At 200 mg/kg, diltiazem resulted in 100% protection. However, all animals appeared mildly lethargic, possibly due to a hypotensive effect of the drug at this dose. The highest dose of diltiazem employed, 300 mg/kg, produced 100% death within 5 to 10 minutes of administration.

TA-3090 afforded 90% protection at a dose of about 10 mg/kg body weight. Unexpectedly, however, no protection was seen at the next higher dose of 30 mg/kg. Equally unexpected was the added observation that nine of the ten animals in this unprotected 30 mg/kg group also died within a matter of 5-15 seconds after shock administration.

Verapamil, while showing some degree of antiseizure activity between 1 and 30 mg/kg, was never able to afford greater than 35% protection in the MES test. At a verapamil dose of 100 mg/kg all animals died prior to MES testing within 5-10 minutes of drug administration.

As shown in Table III, diltiazem, TA-3090, and verapamil were all ineffective in protecting the mice from Metrazol-induced seizures in the MMC test at doses which afforded maximum protection against MES-induced seizures (Table III). This was in contrast to the valproate positive control group (175 mg/kg) which was totally seizure free in the MMC test.

TABLE III

EFFECTS OF DILTIAZEM, TA-3090, AND VERAPAMIL IN THE MAXIMAL METRAZOL CONVULSION TEST[3, 4, 5]

| Dose mg/kg | Diltiazem % Protected[1] | P/T[2] | TA-3090 % Protected | P/T | Verapamil % Protected | P/T |
|---|---|---|---|---|---|---|
| 10 | | | 0 | 0/10 | | |
| 30 | | | | | 0 | 0/10 |
| 100 | 0 | 0/10 | | | | |

[1]Percentage of animals protected from clonic seizures
[2]Number of animals protected/number of animals tested
[3]Negative saline control 0% (0/10)
[4]Negative corn oil control 0% (0/10)
[5]Positive valproate control 100% (10/10) (in 100% corn oil)
Drug not tested at this dose.

Drugs which are effective in the MES test usually are effective in the treatment of generalized tonic-clonic and cortical focal convulsions, while compounds effective in the MMC test are generally effective in preventing absence-type seizures. With reference to FIG. 1 and Table II, this example demonstrates that the benzothiazepine $Ca^{2+}$ channel blockers diltiazem and TA-3090 possess anticonvulsant actions against certain epileptiforms, e.g., generalized tonic-clonic type epileptic seizures (Table II). In particular, diltiazem and TA-3090 appear to be at least equal to phenytoin in efficacy in the prevention of generalized tonic-clonic type seizures.

EXAMPLE 2

This Example shows the time of maximal protection against the appearance of tonic-clonic type epileptic seizures in the MES model of epilepsy following oral administration of diltiazem and TA-3090. The test system and amounts of drug administered were as follows:

Male Swiss Webster mice weighing 20-30 grams as in Example 1 were obtained from Sasco Inc. (Omaha, Nebr.). Animals were housed 5 to a cage for at least one week prior to the study with food and water ad libitum. Mice were randomly divided into 4 groups, weighed, and treated as follows:
GROUP A: Normal saline vehicle as negative control, 1% of body weight, p.o.
GROUP B: Phenytoin as positive control, 100 mg/kg, p.o. (Sigma Chemical Co., Lot #106F0670)
GROUP C: Diltiazem, 200 mg/kg, p.o. (Marion lot #415760)
GROUP D: TA-3090, 30 mg/kg, p.o. (Marion lot #503010)
Each group consisted of 5-10 animals.
The MES tests were carried out as follows: Each drug was orally administered to the mice as indicated above. At the specified time after oral drug administration (15, 30, 60, 90, 120, 180, and 300 minutes), a maximal electroshock (MES)-induced seizure was generated in the mouse by the corneal application of a 40 mA electrical current for 0.2 seconds, as in Example 1. The appearance of tonic hindlimb extensions (THE) exceeding a 90 degree angle to the plane of the body, or death, was considered lack of protection. The time points from 15 to 300 minutes (0.25 to 5 hours) provided a profile of the anticonvulsant activity and potency of each compound and minimized the likelihood of failing to identify slowly absorbed compounds or those with possible anticonvulsant activity in a metabolite. Animals were immediately sacrificed by cervical dislocation either 10 seconds after the appearance of convulsions or 30 seconds post MES, whichever came first. Protection against convulsions were recorded as a quantal (all or none) response.

Dose-response curves for orally administered diltiazem, TA-3090, and phenytoin were generated following the establishment of the time course of their anticonvulsant activity. Each compound was prepared in normal saline and administered at the required dose by oral gavage. Sixty minutes later, seizures were induced in the mouse by MES, as in Example 1, and the appearance or inhibition of THE noted.

Figure 2:
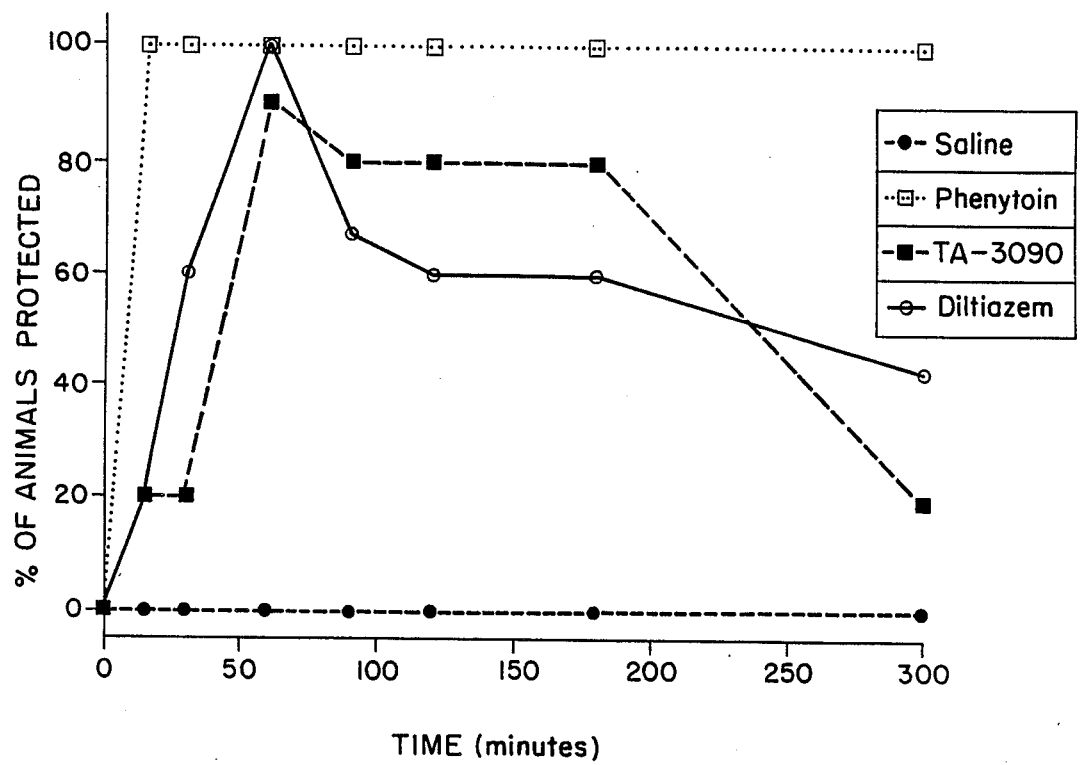
FIG. 2 shows the time course for protection against MES-induced seizures following oral administration of benzothiazepine compounds.

The time course for protection against MES-induced seizures by orally administered diltiazem and TA-3090 are shown in FIG. 2 and Table IV. Also shown are the protective activities of saline and phenytoin administered as negative and positive control compounds, respectively. Each time point in FIG. 2 represents the percentage of animals protected from tonic seizures, calculated from the data in Table IV, at each time point. Five to 10 animals were tested at each time.

As shown in FIG. 2 and Table IV, both diltiazem (200 mg/kg) and TA-3090 (30 mg/kg) protected mice from seizure in a time dependent fashion. The protective effects of both compounds were maximal at 60 minutes post oral administration, with diltiazem being 100% effective and TA-3090 being 90% effective in protecting against THE in the MES test of epilepsy. After three hours, diltiazem and TA-3090 exhibited 60% and 80% protection, respectively. After five hours, diltiazem and TA-3090 still exhibited 43% and 20% protection, respectively. Saline, as expected, wss ineffective as an anticonvulsant. As shown, phenytoin (100 mg/kg, p.o.) was 100% effective in preventing THE at each time point monitored over the full duration of the experiment.

TABLE IV

EFFECTS OF ORAL DILTIAZEM, TA-3090, AND PHENYTOIN IN THE MAXIMAL ELECTROSHOCK CONVULSION TEST

| Time (min.) | Diltiazem[3] % Protected[1] | P/T[2] | TA-3090[4] % Protected | P/T | Phenytoin[5] % Protected | P/T | Saline[6] % Protected | P/T |
|---|---|---|---|---|---|---|---|---|
| 15 | 20 | 1/5 | 20 | 1/5 | 100 | 5/5 | 0 | 0/5 |
| 30 | 60 | 6/10 | 20 | 2/10 | 100 | 5/5 | 0 | 0/5 |
| 60 | 100 | 10/10 | 90 | 9/10 | 100 | 5/5 | 0 | 0/5 |
| 90 | 67 | 4/6 | 80 | 8/10 | 100 | 6/6 | 0 | 0/5 |
| 120 | 60 | 3/5 | 80 | 4/5 | 100 | 5/5 | 0 | 0/5 |
| 180 | 60 | 3/5 | 80 | 4/5 | 100 | 5/5 | 0 | 0/5 |
| 300 | 43 | 3/7 | 20 | 1/5 | 100 | 5/5 | 0 | 0/5 |

[1]Percentage of animals protected from tonic hindlimb seizures
[2]Number of animals protected/number of animals tested
[3]Diltiazem, 200 mg/kg, p.o.
[4]TA-3090, 30 mg/kg, p.o.
[5]Phenytoin, 100 mg/kg, p.o.
[6]Saline, 1% of body weight, p.o.

Figure 3:
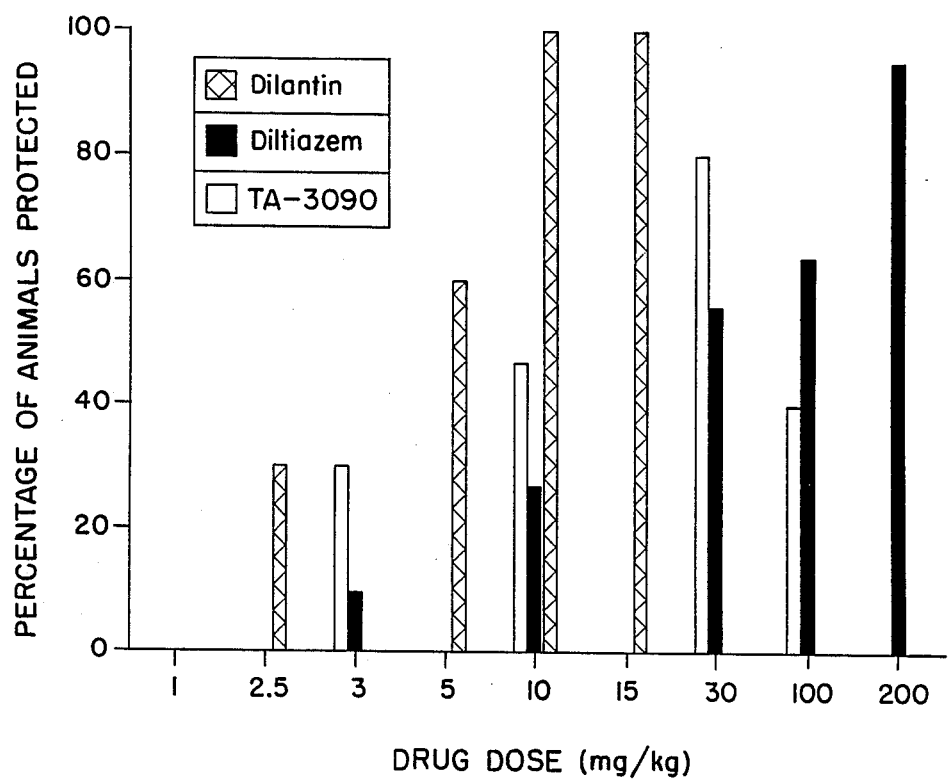
FIG. 3 is a bar graph showing protection from MES-induced seizures after oral administration of benzothiazepine compounds.

Table V and FIG. 3 demonstrate that both diltiazem and TA-3090 were effective in preventing generalized tonic-clonic seizures in a concentration dependent manner after oral administration. Probit analysis of the data revealed $ED_{50}$ values of 29, 9.8, and 3.7 mg/kg for dilitazem, TA-3090, and phnenytoin, respectively. Thus, after oral administration, both diltiazem and TA-3090 were as effective as phenytoin in their ability to protect against MES-induced seizures, although neither diltiazem or TA-3090 were as potent as phenytoin.

The results of these tests clearly show that after oral administration, both diltiazem and TA-3090 have anticonvulsant activity against generalized tonic-clonic type epileptiforms.

TABLE V

EFFECTS OF DILTIAZEM, TA-3090, AND PHENYTOIN IN THE MAXIMAL ELECTROSHOCK CONVULSION TEST[3] ONE HOUR AFTER ORAL ADMINISTRATION

| Dose mg/kg | Diltiazem % Protected[1] | P/T[2] | TA-3090 % Protected | P/T | Phenytoin % Protected | P/T |
|---|---|---|---|---|---|---|
| 0.3 |  |  | 0 | 0/10 |  |  |
| 1 | 0 | 0/10 | 0 | 0/11 | 0 | 0/11 |
| 2.5 |  |  |  |  | 30 | 3/10 |
| 3 | 10 | 1/10 | 30 | 3/10 |  |  |
| 5 |  |  |  |  | 60 | 6/10 |
| 10 | 27 | 4/15 | 47 | 7/15 | 100 | 10/10 |
| 15 |  |  |  |  | 100 | 9/9 |
| 30 | 56 | 5/9 | 80 | 12/15 |  |  |
| 50 |  |  | 40 | 4/10 |  |  |
| 100 | 64 | 9/14 |  |  |  |  |

TABLE V-continued
EFFECTS OF DILTIAZEM, TA-3090, AND PHENYTOIN IN THE MAXIMAL ELECTROSHOCK CONVULSION TEST[3] ONE HOUR AFTER ORAL ADMINISTRATION

| Dose mg/kg | Diltiazem % Protected[1] | P/T[2] | TA-3090 % Protected | P/T | Phenytoin % Protected | P/T |
|---|---|---|---|---|---|---|
| 200 | 95 | 19/20 | | | | |

[1] Percentage of animals protected from tonic hindlimb seizures (THE)
[2] Number of animals protected/number of animals tested
[3] Negative Saline Control 0% (0/25)
  Drug not tested at this dose

EXAMPLE 3

This Example shows the efficacy of various metabolites of diltiazem and TA-3090 in inhibiting seizures induced by maximal electroshock (MES) in mice. Two metabolites of diltiazem, N-monomethyldiltiazem (herein MA) wherein $R_1$ is acetyloxy, $R_2$ is hydrogen and $R_3$ is methyl and desacetytldiltiazem (herein Ml) wherein $R_1$ is hydroxy and $R_2$ and $R_3$ are each methyl, and one metabolite of TA-3090, N-monodemethyl-deacetyl-TA-3090 (herein MB3) wherein $R_1$ is hydroxy, $R_2$ is hydrogen and $R_3$ is methyl, were tested for inhibition of generalized tonic-clonic type seizures.

As in the previous Examples, male Swiss Webster mice weighing 20-30 grams were obtained from Sasco Inc. (Omaha, Nebr.). Animals were housed 5 to a cage for at least one week prior to the study, with food and water ad libitum. Mice were randomly divided into 7 groups, weighed, and treated as follows:
Group 1: TA-3090 (Marion Lot #503010)
Group 2: Diltiazem (Marion Lot #415760)
Group 3: MA, N-monodemethyldiltiazem (Marion Lot #0478049)
Group 4: Ml, Desacetyldiltiazem (Marion Lot #975010)
Group 5: MB3, N-monodemethyl-deacetyl-TA-3090 (Marion Lot #0545078B)
Group 6: Phenytoin (Sigma Chemical Co. Lot #106F0670)
Group 7: Nimodipine (Miles Laboratories Lot #129667E)

The MES test was carried out following intraperitoneal injection of the test compounds. Twenty minutes after drug administration, MES was induced in the mouse by the corneal application of a 40 mA electrical current for 0.2 seconds, as in Example 1. The appearance of tonic hindlimb extensions (THE), or death, was considered lack of protection. Failure of the THE to exceed a 90 degree angle to the plane of the body indicated that the compound could prevent MES-induced seizures. Animals were immediately sacrificed by cervical dislocation either 10 seconds after the appearance of convulsions or 30 seconds post MES, whichever came first.

Protection against convulsions was recorded as a quantal (all or none) response. Test compounds were administered to groups of 9-20 animals. The dose at which 50% of the total number of animals tested were protected ($ED_{50}$) was expressed in mg/kg. The $ED_{50}$ dose was obtained by probit analysis.

Figure 4:
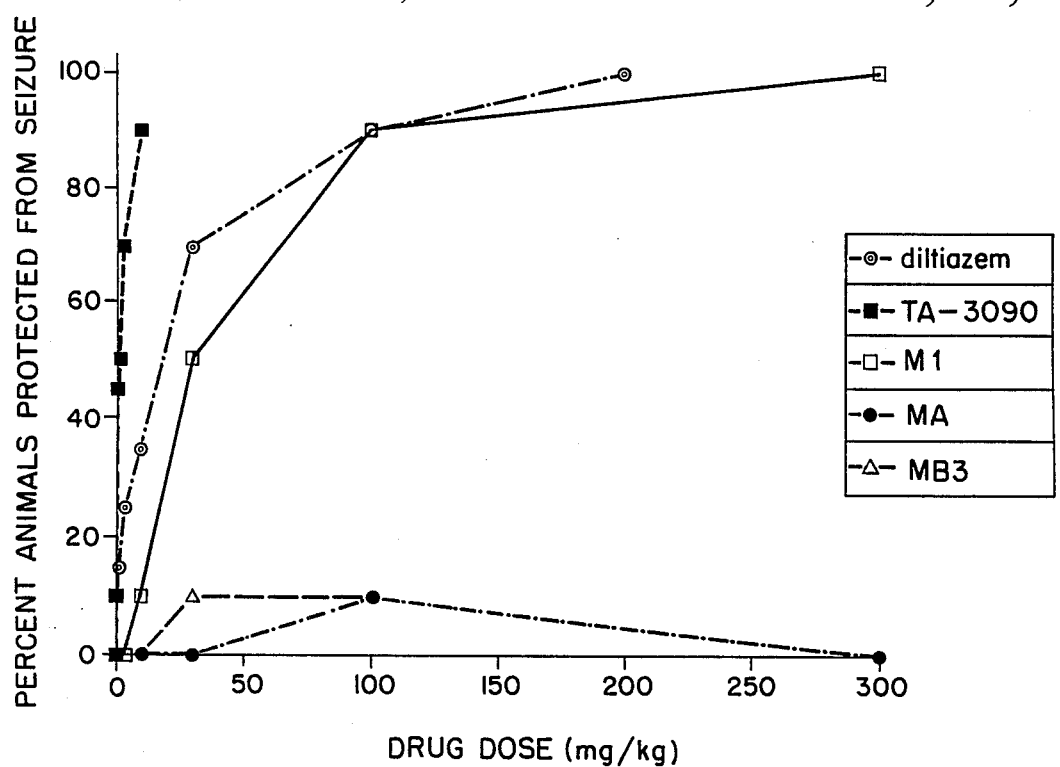
FIG. 4 is a graph showing protection from MES-induced seizures after administration of benzothiazepine compounds and metabolites thereof.

As shown in FIG. 4 and Table VI, the metabolite Ml, diltiazem and TA-3090 each protected the treated mice from seizures in a dose dependent fashion, with the order of potency being TA-3090>diltiazem>Ml. At a dose of 200 mg/kg, diltiazem resulted in 100% protection. Ml, at a dose of 300 mg/kg i.p., produced 90% protection, while TA-3090 afforded 90% protection at a dose of 30 mg/kg i.p. Phenytoin showed complete protection from seizure at a dose of 100 mg/kg i.p. Probit analysis revealed $ED_{50}$ values of 31.06 mg/kg, 10.96 mg/kg, and 0.84 mg/kg for Ml, diltiazem, and TA-3090, respectively. Diltiazem, Ml and TA-3090 appear to be at least equal in efficacy to phenytoin ($ED_{50}=9.5$ mg/kg) in preventing THE in the MES test in the mouse epilepsy model. Ml was approximately three times less potent than phenytoin, but was still able to provide 90% protection.

The metabolites MA and MB3 were only 10% effective at the highest concentrations tested. MA, however, possessed definite toxic central nervous system actions as evidenced by extreme lethargy and abnormal postural positioning of all 10 animals receiving the highest dose (300 mg/kg) as well as the death of 5 animals within 10 minutes of drug administration. Animals treated with the highest dose of MB3 (100 mg/kg) were visibly sedated.

Thirty percent of the animals receiving the dihydropyridine $Ca^{2+}$ channel antagonist nimodipine (100 mg/kg, i.p.) died prior to MES. Of the seven surviving animals, only three were protected from convulsions. Polyethylene glycol (PEG, the nimodipine vehicle control) and the metabolite vehcle control (slightly acidified water) were ineffective as anticonvulsants (data not shown).

The results in this Example demonstrate that the Ml metabolite of diltiazem possesses anticonvulsant activity (FIG. 4, Table VI). MI appears to be about 30 to 50% as potent as diltiazem, but equally effective in the prevention of generalized tonic-clonic type seizures.

Diltiazem and TA-3090 have been shown to have unusually low partition coefficients for CNS activity (P=diltiazem=0.154±0.030, TA-3090=0.781±0.058, octonol/water). Nonetheless, it is believed that diltiazem rapidly penetrates into cerebrospinal fluid (CSF) probably due to its elimination by diffusion into the brain rather than filtration from the CSF by subarachnoid villi and the lack of metabolizing enzymes in the CSF. See, e.g., Naito et al., Arzneimittelforsch 36:25–28, 1986. The data in this Example indicates that a (dimethylamino)ethyl moiety at position 5 of Ml appears to be important for protection from MES-induced seizures. This is evidenced by the lack of anticonvulsant activity of MA and MB3 whch only contain a (monomethylamino)ethyl moiety at this position. It is thus believed that a (dialkylamino)ethyl moiety at position 5 of the benzothiazepine structure is required for anticonvulsant activity of such components.

TABLE VI
EFFECTS OF DILTIAZEM[1], TA-3090[1], M1, MA & MB3 IN THE MAXIMAL ELECTROSHOCK CONVULSION TEST[2][3]

| Dose mg/kg | Diltiazem % Protected[1,4] | P/T[5] | TA-3090 % Protected[1] | P/T |
|---|---|---|---|---|
| 0.03 | | | 0 | 0/10 |
| 0.1 | | | 10 | 2/20 |
| 0.3 | 10 | 2/20 | 45 | 9/10 |
| 1 | 15 | 3/20 | 50 | 10/20 |
| 3 | 25 | 5/20 | 70 | 14/20 |
| 10 | 35 | 7/20 | 90 | 18/20 |
| 15 | | | 50 | 5/10 |
| 20 | | | 40 | 4/10 |
| 30 | 70 | 14/20 | 0 | 0/10 |
| 100 | 90 | 18/20 | | |
| 200 | 100 | 9/9 | | |
| 300 | * | * | | |

TABLE VI-continued

EFFECTS OF DILTIAZEM[1], TA-3090[1], M1, MA & MB3 IN THE MAXIMAL ELECTROSHOCK CONVULSION TEST[2][3]

| Dose mg/kg | MB3[7] % Protected | P/T | MA[8] % Protected | P/T | M1[8] % Protected | P/T |
|---|---|---|---|---|---|---|
| 1 | | | | | | |
| 3 | | | | | 0 | 0/10 |
| 10 | 0 | 0/10 | 0 | 0/10 | 10 | 1/10 |
| 30 | 10 | 1/10 | 0 | 0/10 | 50 | 5/10 |
| 100 | 10[6] | 1/10[6] | 10[6] | 1/10[6] | 90 | 9/10 |
| 300 | | | 0 | 0/10[6] | 100[6] | 9/9 |

[1]Data from Example 1

[2]Negative Saline control (10 ml/kg) 0% (0/25)

[3]Positive Phenytoin Control (20 mg/kg) 100% (10/10)

[4]Percentage of animals protected from tonic hindlimb seizures

[5]Number of animals protected/number of animals tested

[6]Mildly sedate and/or visibly lethargic

[7]Metabolite of TA-3090

[8]Metabolite of diltiazem

*100% death due to drug

Drug not tested at this dose

What is claimed is:

1. A method for ameliorating generalized tonic-colnic type epileptic seizures in mammals comprising systemically administering to a mammal in need of such treatment an effective daily dose of up to 360 mg of a compound having the formula:

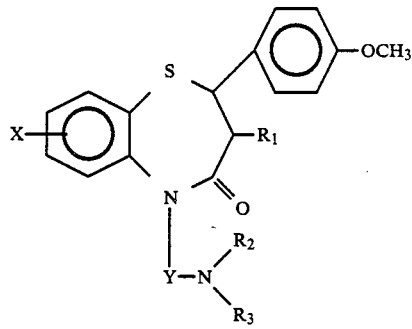

wherein X is hydrogen, a lower straight chain or branched alkyl, hydroxy, a halogen or a lower straight chain or branched alkyl halide; Y is a lower straight chain or branched alkyl; $R_1$ is hydrogen, hydroxyl or acetyloxy; $R_2$ and $R_3$ are each a lower straight chain or branched alkyl or a non-aromatic cycloalkyl, and pharmaceutically acceptable salts thereof.

2. Method according to claim 1 wherein the compound is selected from those in which X is hydrogen or 8-chloro, Y is ethyl, $R_1$ is acetyloxy and $R_2$ and $R_3$ are each a lower alkyl.

3. Method according to claim 2 wherein $R_2$ and $R_3$ are each methyl.

4. Method according to claim 1 wherein the compound is (+)(2S,3S)-3-acetyloxy-5-(2-dimethylaminoethyl)-2,3-dihydro-2-(4-methoxyphenyl)-1,5-benzothiazepin-4-(5H)-one.

5. Method according to claim 1 wherein the compound is (+)(2S,3S)-3-acetoxy-8-chloro-5-(2-dimethylaminoethyl)-2,3-dihydro-2-(4-methoxyphenyl)-1,5-benzothiazepin-4-(5H)-one.

6. Method according to claim 1 wherein the compound is administered in an amount of about 0.5 to 360 mg per day.

7. Method according to claim 1 wherein the compound is administered in an amount of about 30 to 180 mg per day.

8. Method according to claim 1 wherein the compound is administered orally.

9. Method according to claim 8 wherein the compound is administered in a divided dose given 3 to 4 times daily.

10. Method according to claim 1 wherein the compound is administered by injection.

* * * * *